US006294384B1

United States Patent
Dell'Acqua et al.

(10) Patent No.: US 6,294,384 B1
(45) Date of Patent: Sep. 25, 2001

(54) COMPOSITIONS AND METHODS BASED UPON AN ISOFORM OF P53

(75) Inventors: Giorgio Dell'Acqua, Brookline; Michael J. Mann; Victor J. Dzau, both of Newton, all of MA (US)

(73) Assignee: The Brigham and Women's Hospital Inc., Boston, MA (US)

( * ) Notice: Subject to any disclaimer, the term of this patent is extended or adjusted under 35 U.S.C. 154(b) by 0 days.

(21) Appl. No.: 09/414,436

(22) Filed: Oct. 7, 1999

Related U.S. Application Data
(60) Provisional application No. 60/103,849, filed on Oct. 9, 1998.

(51) Int. Cl.⁷ .................................................. C12N 15/63
(52) U.S. Cl. ........................... 435/455; 435/6; 435/69.1; 435/320.1; 435/325; 536/23.1; 536/23.5; 530/350
(58) Field of Search .................................. 530/350, 357.1; 536/23.1, 23.5; 435/6, 69.1, 320.1, 325, 335, 455

(56) References Cited

U.S. PATENT DOCUMENTS

| | | | |
|---|---|---|---|
| 5,573,925 | 11/1996 | Halazonetis | 435/69.7 |
| 5,726,024 | 3/1998 | Kulesz-Martin | 435/7.1 |
| 5,840,579 | 11/1998 | Boeke et al. | 435/325 |
| 5,847,083 | 12/1998 | Halazonetis | 530/358 |
| 6,017,524 | 1/2000 | Roth et al. | 424/93.2 |

OTHER PUBLICATIONS

W. Anderson, Human gene therapy; Apr., 1998, Nature vol. 392:25–30.*
I. Verma, Gene therapy—promises, problems and prospects, Sep. 1997; Nature vol. 389:239–242.*
Y. Hirano et.al.; Roles of p53 Mutation in Cell Line Establishment and Identification of the Minimum Transactivation and Transform Suppression Domains, 1995; Eur J. Cancer, vol. 31B129.*
Haupt et.al.; p53 Mediated Apoptosis in HeLa Cells: Transcription Dependent and Independent Machanisms, 1997; Leukemia 11(Suppl 3): 337–339.*

S. Picksley, Immunochemical analysis of the interaction of p53 with MDM2; fine mapping of the MDM2 binding site on p53 using synthetic peptides, 1994; Oncogene 92523–2529.*
S. Jamal, Raf phosphorylates p53 in vitro and potentiates p53–dependent transcriptional transactivation in vitro; 1995, Oncogene 10, 2095–2101.*
Eck SL & Wilson JM, 1996. Gene–based Thereapy in Goodman & Gilman's The Pharmacological Basis of Therapeutics. McGraw–Hill, 9th Edition, pp 77–101.*
Dell'Acqua, et al., "Identification, Characterization and Functional Studies of a Novel p53 Alternative Splice Product in the Rat," *FASEB Journal,* Abstracts Annual Meeting of The American Societies for Experimental Biology on Biochemistry and Molecular Biology, San Francisco, CA, 13(7):A1480 (1999), abstract No. 852 XP002132830.
Fukuda, et al., "Alternatively–Spliced p53 mRNA in the FAA–HTC1 Rat Hepatoma Cell Line Without the Splice Site Mutations," *Cell Structure and Function* 17(6):427–431 (1992).
Graeber, et al., "Hypoxia–Mediated Selection of Cells with Diminished Apoptotic Potential in Solid Tumours," *Nature* 379:88–91 (1996).
Hulla, et al., "Structure of the Rat p53 Tumor Suppressor Gene," *Nucleic Acids Res.* 21(3):713–717 (1993).
Lamb, et al., "Characterization of the Human p53 Gene," *Molecular and Cell Biology* 6(5):1379–1385 (1986).
Nakai, et al., "Multiple Aberrant Splicing of the p53 Transcript Without Genomic Mutations Around Exon–Intron Junctions in a Case of Chronic Myelogenous Leukaemia in Blast Crisis: A Possible Novel Mechanism of p53 Inactivation," *Brit. J. Haematol.* 87(4):839–842 (1994).
International Search Report for PCT/US99/23319.

* cited by examiner

Primary Examiner—Karen M. Hauda
Assistant Examiner—Richard Schnizer
(74) Attorney, Agent, or Firm—Michael A. Sanzo; Pillsbury Winthrop LLP

(57) ABSTRACT

The present invention is directed to an isoform of the p53 tumor suppressor and to polynucleotides that encode this isoform. The isoform may be used as a marker to indicate that cardiac cells have experienced hypoxia, as would occur during a myocardial infarction. In addition, vectors encoding the isoform may be transfected into cells as a means of regulating proliferation.

20 Claims, 2 Drawing Sheets

MEDSQSDMSIELPLSQETFSCLWKLLPPDDILPTTATGSPNSMEDLFLPQD
VAELLEGPEEALQVSAPAAQEPGTEAPAPVAPASATPWPLSSSVPSQKTY
QGNYGFHLQFLQSGTAKSVMCTYSISLNKLFCQLAKTCPVQLWVTSTPP
PGTRVRAMAIYKKSQHMTEVVRRCPHHERCSDGDGLAPPQHLIRVEGN
PYAEYLDDRQTFRHSVVVPYEPPEVGSDYTTIHYKYMCNSSCMGGMNR
RPILTIITLEDSRSVGVSASACSES

FIG.1 cccctgaagactggataactgtcatggaggattcacagtcggatatgagcatcgagctccctc
tgagtcaggagacattttcatgcttatggaaacttcttcctccagatgatattctgcccaccaca
gcgacagggtcacctaattccatggaagatctgttcctgccccaggatgttgcagagttgttag
aaggcccagaggaagccctccaagtgtcagctcctgcagcacaggaacctggaactgaggc
ccctgcacccgtggcccctgcttcagctacaccgtggcctctgtcatcttccgtcccttctcaaa
aaacttaccaaggcaactatggcttccacctgggcttcctgcagtcagggacagccaagtctg
ttatgtgcacgtactcaatttccctcaataagctgttctgccagctggcgaagacatgccctgtg
cagttgtgggtcacctccacacctccacctggtacccgtgtccgtgccatggccatctacaag
aagtcacaacacatgactgaggtcgtgagacgctgcccccaccatgagcgttgctctgatggt
gacggcctggctcctccccaacatcttatccgggtggaaggaaatccgtatgctgagtatctg
gacgacaggcagacttttcggcacagcgtggtggtaccgtatgagccacctgaggtcggctc
cgactataccactatccactacaagtacatgtgcaacagctcctgcatggggggcatgaaccg
ccggcccatccttaccatcatcacgctggaagactccagatccgtgggcgtgagcgcttcga
gatgttccgagagctgaatgaggccttggaattaaaggatgcccgtgctgccgaggagtcag
gagacagcagggctcactccagctacccgaagaccaagaagggccagtctacgtcccgcca
taaaaaaccaatgatcaagaaagtggggcctgactcagactgacagcctctgcatcctgtccc
catcaccagcctccccgtcccctccttcttgccatttatgactttagggcttgttatgagagct
gacaagacaatgctagtcccttcactgccttttttaccttgtagatagtactcggcccctctat
gcaaactggttcctggcccagattggggaatgggttggtagttgctgggtctctgctggtcca
gcgaaatcctatccggtcagttgttggacctggcacctacagtgaaatttcaccccaccccacc
gcctgtaagattctatcttgggccctcatacgatctgtatcctccaggacccatttcctccactct
gcaaagcctgtctgcatttatccatcccccaccctctccctctttttatatatttttatatatccaa
tttcttattttacaa

FIG.2

MEEPQSDPSVEPPLSQETFSDLWKLLPENNVLSPLPSQAMDDLMLS
PDDIEQWFTEDPGPDEAPRMPEAAPPVAPAPAAPTPAAPAPAPSWP
LSSSVPSQKTYQGSYGFRLGFLHSGTAKSVTCTYSPALNKMFCQLA
KTCPVQLWVDSTPPPGTRVRAMAIYKQSQHMTEVVRRCPHHERCS
DSDGLAPPQHLIRVEGNLRVEYLDDRNTFRHSVVVPYEPPEHCPTT
PAPLPSQRRNHWMENISPFRSVGVSASRCSES

FIG.3 gtctagagccaccgtccagggagcaggtagctgctgggctccggggacactttgcgttcgggctgg
gagcgtgctttccacgacggtgacacgcttccctggattggcagccagactgccttccgggtcactgc
catggaggagccgcagtcagatcctagcgtcgagccccctctgagtcaggaaacattttcagacctat
gaaactacttcctgaaaacaacgttctgtccccttgccgtcccaagcaatggatgatttgatgctg
cccggacgatattgaacaatggttcactgaagacccaggtccagatgaagctcccagaatgccagag
gctgctcccccgtggcccctgcaccagcagctcctacaccggcggcccctgcaccagccccctcct
ggcccctgtcatcttctgtcccttcccagaaaacctaccagggcagctacggtttccgtctgggcttct
gcattctgggacagccaagtctgtgacttgcacgtactcccctgccctcaacaagatgttttgccaact
ggccaagacctgccctgtgcagctgtggttgattccacaccccgcccggcacccgcgtccgcgcc
atggccatctacaagcagtcacagcacatgacggaggttgtgaggcgctgcccccaccatgagcgct
gctcagatagcgatggtctggcccctcctcagcatcttatccgagtggaaggaaatttgcgtgtggagt
atttggatgaeagaaacacttttcgacatagtgtggtggtgcccatgagccgcctgagcactgcccaa
caacaccagctcctctccccagccaaagaagaaaccactggatggagaatatttcacccttcagatcc
gtgggcgtgagcgcttcgagatgttccgagagctgaatgaggccttggaactcaaggatgcccaggc
tgggaaggagccagggggggagcagggctcactccagccacctgaagtccaaaaagggtcagtcta
cctcccgccataaaaaactcatgttcaagacagaagggcctgactcagactga

SEQUENCE LISTING

<160> NUMBER OF SEQ ID NOS: 5

<210> SEQ ID NO 1
<211> LENGTH: 271
<212> TYPE: PRT
<213> ORGANISM: Rattus norvegicus

<400> SEQUENCE: 1

```
Met Glu Asp Ser Gln Ser Asp Met Ser Ile Glu Leu Pro Leu Ser Gln
 1               5                  10                  15

Glu Thr Phe Ser Cys Leu Trp Lys Leu Leu Pro Pro Asp Asp Ile Leu
            20                  25                  30

Pro Thr Thr Ala Thr Gly Ser Pro Asn Ser Met Glu Asp Leu Phe Leu
        35                  40                  45

Pro Gln Asp Val Ala Glu Leu Leu Glu Gly Pro Glu Glu Ala Leu Gln
    50                  55                  60

Val Ser Ala Pro Ala Ala Gln Glu Pro Gly Thr Glu Ala Pro Ala Pro
65                  70                  75                  80

Val Ala Pro Ala Ser Ala Thr Pro Trp Pro Leu Ser Ser Ser Val Pro
                85                  90                  95

Ser Gln Lys Thr Tyr Gln Gly Asn Tyr Gly Phe His Leu Gly Phe Leu
            100                 105                 110

Gln Ser Gly Thr Ala Lys Ser Val Met Cys Thr Tyr Ser Ile Ser Leu
        115                 120                 125

Asn Lys Leu Phe Cys Gln Leu Ala Lys Thr Cys Pro Val Gln Leu Trp
    130                 135                 140

Val Thr Ser Thr Pro Pro Pro Gly Thr Arg Val Arg Ala Met Ala Ile
145                 150                 155                 160

Tyr Lys Lys Ser Gln His Met Thr Glu Val Val Arg Arg Cys Pro His
```

```
                            165                 170                 175
        His Glu Arg Cys Ser Asp Gly Asp Gly Leu Ala Pro Pro Gln His Leu
                        180                 185                 190

Ile Arg Val Glu Gly Asn Pro Tyr Ala Glu Tyr Leu Asp Asp Arg Gln
                    195                 200                 205

Thr Phe Arg His Ser Val Val Pro Tyr Glu Pro Pro Glu Val Gly
                210                 215                 220

Ser Asp Tyr Thr Thr Ile His Tyr Lys Tyr Met Cys Asn Ser Ser Cys
        225                 230                 235                 240

Met Gly Gly Met Asn Arg Arg Pro Ile Leu Thr Ile Ile Thr Leu Glu
                        245                 250                 255

Asp Ser Arg Ser Val Gly Val Ser Ala Ser Ala Cys Ser Glu Ser
                    260                 265                 270

<210> SEQ ID NO 2
<211> LENGTH: 1415
<212> TYPE: DNA
<213> ORGANISM: Rattus norvegicus

<400> SEQUENCE: 2
cccctgaaga ctggataact gtcatggagg attcacagtc ggatatgagc atcgagctcc      60
ctctgagtca ggagacattt tcatgcttat ggaaacttct tcctccagat gatattctgc     120
ccaccacagc gacagggtca cctaattcca tggaagatct gttcctgccc aggatgttg      180 cagagttgtt agaaggccca gaggaagccc tccaagtgtc agctcctgca gcacaggaac     240
ctggaactga ggcccctgca cccgtggccc tgcttcagc tacaccgtgg cctctgtcat      300
cttccgtccc ttctcaaaaa acttaccaag gcaactatgg cttccacctg gcttcctgc     360 agtcagggac agccaagtct gttatgtgca cgtactcaat tccctcaat aagctgttct     420 gccagctggc gaagacatgc cctgtgcagt tgtgggtcac ctccacacct ccacctggta     480
cccgtgtccg tgccatggcc atctacaaga agtcacaaca catgactgag gtcgtgagac     540 gctgcccca ccatgagcgt tgctctgatg gtgacgcct ggctcctccc caacatctta      600
tccgggtgga aggaaatccg tatgctgagt atctggacga caggcagact tttcggcaca     660
gcgtggtggt accgtatgag ccacctgagg tcggctccga ctataccact atccactaca     720
agtacatgtg caacagctcc tgcatggggg gcatgaacgc cggcccatcc ttaccatcat     780
cacgctggaa gactccagat ccgtgggcgt gagcgcttcg agatgttccg agagctgaat     840
gaggccttgg aattaaagga tgcccgtgct gccgaggagt caggagacag cagggctcac     900
tccagctacc cgaagaccaa gaagggccag tctacgtccc gccataaaaa accaatgatc     960
aagaaagtgg ggcctgactc agactgacag cctctgcatc ctgtccccat caccagcctc    1020
cccgtcccct cctttcttgc cattttatga ctttagggct tgttatgaga ctgacaaga    1080 caatgctagt cccttcactg cctttttta ccttgtagat agtactcggc cccctctatg    1140
caaactggtt cctggcccag attggggaat gggttggtag ttgctgggtc tctgctggtc    1200
cagcgaaatc ctatccggtc agttgttgga cctggcacct acagtgaaat tcacccccac    1260
cccaccgcct gtaagattct atcttgggcc ctcatacgat ctgtatcctc caggacccat    1320
ttcctccact ctgcaaagcc tgtctgcatt tatccatccc ccaccctct ccctcttttt     1380 atctcttttt atatatccaa tttcttattt tacaa                               1415

<210> SEQ ID NO 3
<211> LENGTH: 261
```

```
<212> TYPE: PRT
<213> ORGANISM: Homo sapiens

<400> SEQUENCE: 3

Met Glu Glu Pro Gln Ser Asp Pro Ser Val Glu Pro Pro Leu Ser Gln
  1               5                  10                  15

Glu Thr Phe Ser Asp Leu Trp Lys Leu Leu Pro Glu Asn Asn Val Leu
             20                  25                  30

Ser Pro Leu Pro Ser Gln Ala Met Asp Asp Leu Met Leu Ser Pro Asp
         35                  40                  45

Asp Ile Glu Gln Trp Phe Thr Glu Asp Pro Gly Pro Asp Glu Ala Pro
     50                  55                  60

Arg Met Pro Glu Ala Ala Pro Pro Val Ala Pro Ala Pro Ala Ala Pro
 65                  70                  75                  80

Thr Pro Ala Ala Pro Ala Pro Ala Pro Ser Trp Pro Leu Ser Ser Ser
                 85                  90                  95

Val Pro Ser Gln Lys Thr Tyr Gln Gly Ser Tyr Gly Phe Arg Leu Gly
                100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
        130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

His Cys Pro Thr Thr Pro Ala Pro Leu Pro Ser Gln Arg Arg Asn His
225                 230                 235                 240

Trp Met Glu Asn Ile Ser Pro Phe Arg Ser Val Gly Val Ser Ala Ser
                245                 250                 255

Arg Cys Ser Glu Ser
            260

<210> SEQ ID NO 4
<211> LENGTH: 1070
<212> TYPE: DNA
<213> ORGANISM: Homo sapiens

<400> SEQUENCE: 4
gtctagagcc accgtccagg gagcaggtag ctgctgggct ccggggacac tttgcgttcg    60
ggctgggagc gtgctttcca cgacggtgac acgcttccct ggattggcag ccagactgcc   120
ttccgggtca ctgccatgga ggagccgcag tcagatccta gcgtcgagcc ccctctgagt   180
caggaaacat ttcagacct atggaaacta cttcctgaaa acaacgttct gtccccttg    240 ccgtcccaag caatggatga tttgatgctg tccccggacg atattgaaca atggttcact   300
gaagacccag gtccagatga agctcccaga atgccagagg ctgctccccc cgtggcccct   360
gcaccagcag ctcctacacc ggcggcccct gcaccagccc ctcctggcc cctgtcatct   420 tctgtccctt cccagaaaac ctaccagggc agctacggtt ccgtctgggg cttcttgcat   480
```

```
tctgggacag ccaagtctgt gacttgcacg tactcccctg ccctcaacaa gatgttttgc      540
caactggcca agacctgccc tgtgcagctg tgggttgatt ccacaccccc gcccggcacc      600
cgcgtccgcg ccatggccat ctacaagcag tcacagcaca tgacggaggt tgtgaggcgc      660
tgcccccacc atgagcgctg ctcagatagc gatggtctgg cccctcctca gcatcttatc      720
cgagtggaag gaaatttgcg tgtggagtat ttggatgaca gaaacacttt tcgacatagt      780
gtggtggtgc cctatgagcc gcctgagcac tgcccaacaa caccagctcc tctccccagc      840
caaagaagaa accactggat ggagaatatt tcacccttca gatccgtggg cgtgagcgct      900
tcgagatgtt ccgagagctg aatgaggcct tggaactcaa ggatgcccag gctgggaagg      960
agccaggggg gagcagggct cactccagcc acctgaagtc caaaaagggt cagtctacct     1020
cccgccataa aaaactcatg ttcaagacag aagggcctga ctcagactga               1070

<210> SEQ ID NO 5
<211> LENGTH: 13
<212> TYPE: PRT
<213> ORGANISM: Rattus norvegicus

<400> SEQUENCE: 5

Arg Ser Val Gly Val Ser Ala Ser Ala Cys Ser Glu Ser
 1               5                  10
```

COMPOSITIONS AND METHODS BASED UPON AN ISOFORM OF P53

CROSS REFERENCE TO RELATED APPLICATIONS

The present application claims the benefit of U.S. provisional application No. 60/103,849, filed on Oct. 9, 1998 (now abandoned).

FIELD OF THE INVENTION

The present invention is directed to an isoform of p53 and to polynucleotides encoding this isoform. The invention also encompasses a variety of compositions and methods relating to the isoform and polynucleotides.

BACKGROUND OF THE INVENTION

P53 is a tumor suppressor that plays a central role in arresting cell growth and inducing programed cell death. Mutations of p53 are the most common genetic abnormality identified in human malignancies. Despite the significance of p53 as a regulator of cellular growth/death and its apparent role in human disease, the details regarding its biological actions remain relatively obscure.

One mechanism by which p53 is believed to act is through the "transactivation," or the coordinated turning on, of genes in response to stimuli such as cellular stress. Transactivation depends upon the ability of the p53 protein to bind to specific regions of DNA (p53 responsive elements) that are within promoter sequences adjacent to target genes. This binding may lead to either an enhancement or inhibition of target gene expression. In addition, it is believed that p53 may mediate changes in cell behavior through other mechanisms that are independent of its ability to bind DNA.

The p53 protein is itself regulated both by changes in its state of phosphorylation and by intracellular localization. In addition, it has recently become clear that there are a family of proteins, structurally and functionally related to p53, that may play a role in regulating its activity. Among these proteins are at least two truncated forms of the protein that result from alternative splicing of the messenger RNA (mRNA) encoding the C-terminal end of the native protein. Identifying new isoforms of p53 and defining how they affect cellular activity may lead to new ways of regulating cell growth and, eventually, to new diagnostic and therapeutic procedures.

SUMMARY OF THE INVENTION

The present invention is based upon the discovery of a new isoform of p53 that is truncated to eliminate a substantial portion of the C-terminal end of the protein. The isoform is useful as a marker of myocardial infarction and in the control of cellular proliferation both in vitro and in vivo.

In its first aspect, the invention is directed to a substantially purified isoform of p53 (designated "p35") consisting essentially of the amino acid sequence shown in FIG. 1 (SEQ ID NO:1). The term "consisting essentially of" is meant to encompass proteins having exactly the same amino acid sequence as that shown in the figure, as well as proteins with differences that are not substantial as evidenced by their retaining the basic, qualitative functional properties of p35. A "substantially purified" isoform is one that has been separated from other accompanying biological components and will typically comprise at least 85% of a sample, with greater percentages being preferred. Many means are available for assessing the purity of a protein within a sample, including analysis by polyacrylamide gel electrophoresis, chromatography and analytical centrifugation. One preferred method for assessing the purity of p53 is by performing Western blots using an antibody directed against epitopes of p53 retained in p35. The present isoform should appear in such blots as a band at a position characteristic of a protein with a molecular weight of about 35,000.

The invention also encompasses antibodies that are made by a process involving the injection of a preparation of the p35 isoform into an animal capable of antibody production. These antibodies may be either polyclonal or monoclonal. In the latter case, it is preferred that antibody be made by a process involving the injection of a pharmaceutically acceptable preparation into a mouse, followed by fusing mouse spleen cells with myeloma cells.

The invention is also directed to a substantially pure polynucleotide consisting essentially of a nucleotide sequence encoding the p35 isoforn having the amino acid sequence shown in FIG. 2 (SEQ ID NO:2); expression vectors comprising a distinct coding element consisting essentially of such polynucleotides; and host cells transformed with such vectors. A "distinct coding element" refers to the portion of an expression vector responsible for determining the amino acid sequence of an expressed protein. The invention includes all such elements producing proteins corresponding to the amino acid sequence shown in FIG. 1 as well as other proteins that do not differ substantially in terms of structure and function. Also included in the invention is the recombinant p53 isoform made by the host cells described above. The recombinant protein may be isolated using standard techniques, including affinity chromatography with antibodies against epitopes of p53 retained in p35. In a preferred embodiment, the polynucleotide encoding p35 consists essentially of the nucleotide sequence shown in FIG. 2. This polynucleotide may be used in vectors for expressing the isoform, in host cells transformed with such vectors, and in the production of recombinant p35.

In another embodiment, the present invention is directed to a substantially purified human p53 isoform in which the C-terminal portion of the protein has been eliminated. The deleted amino acids correspond to those encoded by exon 7 and by exons corresponding to amino acids lying C-terminal to exon 7. Preferably, the human isoform consists essentially of the amino acid sequence shown in FIG. 3 (SEQ ID NO:3). Antibodies made by injecting a preparation of this isoform into an animal capable of producing antibodies are included in the invention, as are substantially purified polynucleotides encoding the isoform. A polynucleotide encoding human p35 may be used as a distinct coding element in an expression vector. The preferred polynucleotide consists essentially of the nucleotide sequence shown in FIG. 4 (SEQ ID NO:4). Also preferred are vectors which incorporate this particular sequence as a distinct coding element and the host cells and recombinant p53 produced using these vectors.

In another embodiment, the present invention is directed to methods for controlling the proliferation of cells using any of the p35 isoforms or polynucleotides discussed above. The preferred method for controlling proliferation is to transfect cells with a vector capable of expressing p35 in the target cells. Thus, the vector should typically have a p35 coding sequence operably linked to a promoter responsive in the cells being transfected. The procedure may be used either in vitro or in vivo. When used in vitro, any means of transfection may be used including calcium phosphate precipitation, liposome-mediated transfection, electroporation, microinjection, etc. Preferred methods for introducing DNA into cells in vivo include transfection using cationic liposomes (e.g., as described in U.S. Pat. No. 5,676,954 or U.S. Pat. No. 4,897,355); using a particular cationic lipid (e.g., as discussed in 5,703,055); or by injecting DNA directly into tissue (e.g., as discussed in U.S. Pat. No. 5,589,466 or U.S. Pat. No. 5,580,859).

BRIEF DESCRIPTION OF THE FIGURES

FIG. 1: FIG. 1 shows the amino acid sequence of a p53 isoform (p35) derived from rat cardiac myocytes. This sequence is designated as SEQ ID NO: 1 in the Sequence Listing FIG. 2: FIG. 2 shows the cDNA sequence (SEQ ID NO:2) obtained by reverse transcription of RNA extracted from rat cardiac myocytes. The corresponding amino acid sequence is shown in FIG. 1.

FIG. 3: FIG. 3 shows the amino acid sequence of human p35 (SEQ ID NO:3).

FIG. 4: FIG. 4 shows the nucleotide sequence of human p35. This is designated as SEQ ID NO:4.

DETAILED DESCRIPTION OF THE INVENTION

The present invention is directed to an isoform of p53, genetic sequences encoding this isoform and methods for regulating cell proliferation using the isoform. The amino acid sequence of rat p35 is shown in FIG. 1 (SEQ ID NO:1) and the amino acid sequence of its human counterpart is shown in FIG. 3 (SEQ ID NO:3). FIGS. 2 and 4 (SEQ ID NOs: 2 a and 4) are the preferred polynucleotide sequences encoding the proteins.

It will be understood that the present invention encompasses not only sequences identical to those shown in the figures, but also sequences that are essentially the same as evidenced by proteins retaining their basic functional characteristics. For example, it is well known that techniques such as site-directed mutagenesis may be used to introduce variations into a protein's structure. Variations in p35 introduced by this or by a similar method are encompassed by the invention provided that the resulting protein retains its basic biological properties, particularly with respect to its ability to regulate cellular growth.

I. Nucleic Acid Sequences Coding for p35

DNA sequences coding for p35 may be obtained from any tissue or cellular source which expresses the gene. The cells used may be either cultured cells that have not undergone transformation or cell lines specifically engineered to express the isoform. Many methods are available for isolating DNA sequences and may be adapted for the isolation of p35 (see, e.g., Sambrook et al., *Molecular Cloning : A Laboratory Manual*, 2nd ed., Cold Spring Harbor Press (1989)). One preferred method is to screen a CDNA library that has been prepared by reverse transcribing mRNA isolated from tissues or cells known to express p35. The library may be prepared from, for example, rat or human cardiac myocytes. Probes for screening may be synthesized based upon the sequences shown in the figures. In general, probes should be at least 14 nucleotides long and should, preferably, be selected from a region believed to be unique to p35.

Alternatively, the polymerase chain reaction (PCR) may be used directly on reverse transcribed RNA to amplify the p35 sequence. Primers for the PCR reaction may be constructed using the sequences shown in FIG. 1 or 2 and amplification products may be sequenced to confirm that p35 cDNA has been obtained.

II. Production and Isolation of Recombinant p35

In order to express recombinant p35, DNA encoding the structural sequence of the protein must be placed in a vector containing transcriptional and translational signals recognizable by an appropriate host. The cloned p35 sequence, preferably in double-stranded form, is inserted into an expression vector in an operable linkage (ie., it is positioned so as to be under the control of regulatory sequences found in the vector and in such a manner that mRNA is produced which is translated into the p35 amino acid sequence).

Expression of p35 in different hosts may result in different post-translational modifications that can, potentially, alter the properties of the protein. Preferably, nucleic acid encoding p35 is expressed in eukaryotic cells, especially mammalian cells. These cells provide post-translational modifications which, inter alia, aid in the correct folding of proteins. Mammalian cells that can be used include, without limitation, NIH-3T3 cells, CHO cells, HeLA cells, LM(tk-) cells, etc. Vectors for each of these various cell types are well known in the art (see, e.g., Sambrook et al, supra). Preferred eukaryotic promoters include those of the mouse metallothionein I gene; the TK promoter of Herpes virus; the SV40 early promoter; and the CMV early promoter. Some examples of suitable prokaryotic promoters include those capable of recognizing T4 polymerases, the $P_R$ and $P_L$ promoters of bacteriophage lambda, and the trp, recA, heat shock and lacZ promoters of *E. coli*.

Expression vectors may be introduced into host cells by methods such as calcium phosphate precipitation, microinjection, electroporation, or viral transfer and cells expressing p35 can be selected using methods well known in the art. One simple method for confirming the presence of p35 nucleic acid in cells is to perform PCR amplification using primers selected based upon the sequences shown in FIG. 2 or 4.

Recombinant p35 protein may be purified using standard techniques well known in the art. These may include filtration, precipitation, chromatography, and electrophoretic methods. Purity can be assessed by performing electrophoresis on a polyacrylamide gel and visualizing proteins using standard staining techniques. Western blots may also be used to identify p35 using an antibody to p53 that recognizes an epitope conserved in the isoform.

III. Antibodies to P35

The present invention is also directed to antibodies made using the p35 isoform. The process for producing such antibodies may involve either injecting the p35 protein itself into an appropriate animal or injecting short peptides made to correspond to different regions of the protein. The peptides should be at least 5 amino acids in length and should, preferably, be selected from regions believed to be unique to the protein. Methods for making and detecting antibodies are well known to those of skill in the art as evidenced by standard reference works such as: Harlow, et al, *Antibodies, A Laboratory Manual*, Cold Spring Harbor Laboratory, NY (1988); Klein, *Immunology: The Science of Self-Nonself Discrimination*, (1982); Kennett, et al., *Monoclonal Antibodies and Hybridomas: A New Dimension in Biological Analyses*, (1980); and Campbell, "Monoclonal Antibody Technology," in *Laboratory Techniques in Biochemistry and Molecular Biology*, (1984)).

"Antibody," as used herein, is meant to include intact molecules as well as fragments which retain their ability to bind to antigen (e.g., Fab and F(ab')$_2$ fragments). These fragments are typically produced by proteolytically cleaving intact antibodies using enzymes such as papain (to produce Fab fragments) or pepsin (to produce F(ab')$_2$ fragments). The term "antibody" also refers to both monoclonal antibodies and polyclonal antibodies. Polyclonal antibodies are derived from the sera of animals immunized with the antigen. Monoclonal antibodies can be prepared using hybridoma technology (Kohler, et al., *Nature* 256:495 (1975); Hammerling, et al., in: *Monoclonal Antibodies and T-Cell Hybridomas*, Elsevier, N.Y., pp. 563–681 (1981)). In general, this technology involves immunizing an animal, usually a mouse, with either intact p35 or a fragment derived from p35. The splenocytes of the immunized animals are extracted and fused with suitable myeloma cells, e.g., $SP_2$ O cells. After fusion, the resulting hybridoma cells are selectively maintained in HAT medium and then cloned by limiting dilution (Wands, et al., *Gastroenterology* 80:225–232 (1981)). The cells obtained through such selection are then assayed to identify clones which secrete antibodies capable of binding to p35.

The antibodies or fragments of antibodies of the present invention may be used to detect the presence of p35 protein in any of a variety of immunoassays. For example, antibodies may be used in radioimmunoassays or in immnunometric assays, also known as "two-site" or "sandwich" assays (see Chard, "An Introduction to Radioimmune Assay and Related Techniques," in: *Laboratory Techniques in Biochemistry and Molecular Biology*, North Holland Publishing Co., NY (1978)). In a typical immunometric assay, a quantity of unlabeled antibody is bound to a solid support that is insoluble in the fluid being tested, e.g. blood, lymph, cellular extracts, etc. After the initial binding of antigen to immobilized antibody, a quantity of detectably labeled second antibody (which may or may not be the same as the first) is added to permit detection and/or quantitation of bound antigen (see e.g., *Radioimmune Assay Method*, Kirkham, et al., Ed. pp. 199–206, E&S Livingstone, Edinburgh (1970)). Many variations of these types of assays are known in the art and may be employed for the detection of p35.

Antibodies to p35 may also be used in the purification of the protein (see generally, Dean, et al., *Affinity Chromatography, A Practical Approach*, IRL Press (1986)). Typically, antibody is immobilized on a chromatographic matrix such as Sepharose, 4B. The matrix is then packed into a column and the preparation containing p35 is passed through under conditions that promote binding, e g., under conditions of low salt. The column is then washed and bound p35 is eluted using a buffer that promotes dissociation from antibody, e.g. buffer having an altered pH or salt concentration. The eluted p35 may be transferred into a buffer of choice, e.g., by dialysis and then either stored or used directly.

Antibodies may also be used in Western blots designed to detect p35. For these types of assays, antibody may be used which has either been developed specifically to react with p35 or which reacts with an epitope of p53 that is retained in the p35 isoform. The p35 protein will appear on gels as a protein with a molecular weight of about 35,000.

IV. Uses of the Present Invention

It has been discovered that the p35 isoform is normally expressed in cardiac cells in an amount comparable to p53. However, when cells are deprived of oxygen for 24 hours, the p35 protein is lost to a substantial extent. Hypoxia of this nature would be expected to occur in patients that have experienced a myocardial infarction and assays of p35 may therefore be used diagnostically to determine whether a myocardial infarction has occurred. The assays may take the form of Western blots as discussed above or, alternatively, the assays may be designed to quantitate the extent to which p35 cDNA is present in a preparation. Such assays may be performed using techniques such as reverse transcription PCR. The proteins and polynucleotides discussed above would be used as controls in such assays and antibodies to p35 could be used in assays involving Western blots.

An alternative use of p35 is in the control of cellular proliferation. This may be accomplished by transfecting cells with a vector designed to express p35. In some fibroblast cells p35 enhances p53 transactivation whereas in other cells, e.g., cardiac myocytes, p35 inhibits p53 transactivation. Thus, p35 may either promote or inhibit cellular growth. If desired, vectors expressing p35 may be co-transfected with vectors expressing p53. Similarly, a single vector expressing both p53 and p35 may be introduced into cells. Introduction into cells that are proliferating abnormally, e.g., malignant cells, may be used as a technique for arresting or retarding uncontrolled cell growth.

EXAMPLES

I. Isolation of p35 and Structural Determination

P35 was isolated from rat cardiac myocytes using reverse transcription-polymerase chain reaction (RT-PCR) analysis of RNA. In addition to the expected amplified sequence from the wild type p53 MRNA, a second amplicon was obtained. DNA sequencing revealed that this amplicon bore 100% homology to the p53 sequence, but lacked the coding regions corresponding to exons 7 and 8 in the wild type protein. The alternative splice produced a frame shift in the DNA reading sequence, introducing 13 new amino acids in the C-terminus that were then followed by a stop codon. The 13 new amino acids are: RSVGVSASACSES (SEQ ID NO:5). In vitro transcription of this alternative cDNA sequence followed by in vitro translation using a rabbit reticulocyte extract yielded a 35 Kda protein, termed p35, visualized by autoradiography and recognized on immunoblot by monoclonal antibody against an epitope in the conserved core domain of p53 (Pab 240). Overexpression of the cloned cDNA in Cos-7 cells also produced a 35 Kda protein recognized by the same monoclonal antibody. This p35 was used as a positive control to verify the presence of the protein in both adult and neonatal cardiomyocytes in which the original mRNA had been detected. This variant p53 protein, however, was not detected in H9C2, an embryonic cardiomyocyte cell line, suggesting that expression of the protein is differentially regulated during cardiac embryogenesis and differentiation. This suggests that the isoform plays a role in regulating the differentiated state of the cell.

The structure of p35 predicted by its cDNA sequence suggested that disruption of the known DNA-binding region would result in a lack of DNA binding activity. Co-transfection of p35 with a plasmid that expressed the reporter gene luciferase under the control of a p53 responsive element in cells that do not express wild type p53, confirmed that p35 had, in fact, lost p53-like transactivation activity. Complete loss of the C-terminal region also suggested that p35 would be incapable of forming either homodimers or heterodimers, since the dimerization domain is located in this end of the wild type protein. Results of experiments utilizing both a yeast two-hybrid system, as well as immunoprecipitation techniques were consistent with this interpretation of p35 structure, ie., dimerization of two p35 proteins or of p35 and p53 could not be achieved. These findings suggest that p35 may function by interacting with other proteins known to bind to the retained N-terminal region of wild type p53.

II. Functional Studies

It was found that the level of p35 protein measured by Western blotting in cardiac myocytes was comparable to the level of wild type p53 at baseline, but p35 decreased significantly after twenty-four hours of hypoxia p35 may therefore play a role in mediating the hypoxia-induced apoptosis observed in these cells, possibly by releasing p53 from an inhibited state under normoxic conditions. Moreover, co-transfection of these cultured cardiac cells with the luciferase/p53 responsive element plasmid together with plasmids that expressed either p35, wild type p53, or both indicated that p35 can decrease wild type p53-dependent transactivation, suggesting a role for p35 in regulating this p53 pathway.

Overexpression of p35 was carried out in p53 knockout fibroblasts that do not express wild type p53. p35 was found to be localized mainly in the cytoplasm of these cells, as assessed by imnunocytochemistry and Western blotting of cytoplasmic and nuclear extracts. In contrast, wild type p53, when overexpressed in these cells due to transfection with a wild type p53 plasmid, was subject to strong nuclear localization. These findings are consistent with the hypothesized role of p35 in interacting with cytoplasmic proteins, as opposed to the activity of p53 in directly modulating gene activity in the nucleus.

Transactivation studies in the p53−/−fibroblasts, utilizing a p53 responsive element/luciferase plasmid co-transfected together with either p35, wild type p53 or both, again confirmed the lack of intrinsic p35 transactivation activity. However, p35 was able to increase the transactivation achieved through co-transfection with wild type p53. These data were consistent with both experiments in which the p53−/−cells were transfected with either wild type p53, p35, or both. The combination of p35 with wild type p53 produced a significantly enhanced inhibition of thymidine incorporation (a reflection of DNA synthesis and cell growth) after twenty-four hours compared to wild type p53 alone.

The results in growing cells differed markedly from data indicating the inhibitory activity of p35 on p53 transactivation in terminally differentiated, non-growing cardiac myocytes. These observations suggest that p35 is capable of a dual regulatory behavior, enhancing p53 transactivation in some cells under certain conditions while inhibiting transactivation under other circumstances. Such a dual role may allow p35 to act as a switch, regulating the alternative activities of wild type p53, i.e., arresting cell growth at certain times, while inducing cell death at others.

All references cited are fully incorporated by reference. Having now fully described the invention, it will be understood by those of skill in the art that the invention may be performed within a wide and equivalent range of conditions, parameters, and the like, without affecting the spirit or scope of the invention or any embodiment thereof.

---

What is claimed is:

1. An isolated isoform of p53, consisting of the amino acid sequence of SEQ ID NO:1.

2. An isolated polynucleotide, wherein said polynucleotide consists of a nucleotide sequence encoding the isoform of claim 1.

3. A vector for expressing a p53 isoform, comprising a distinct coding element consisting of the polynucleotide of claim 2.

4. A host cell transformed in vitro with the vector of claim 3.

5. The Recombinant p53 isoform produced by the host cell of claim 4.

6. The polynucleotide of claim 2, wherein said polynucleotide consists of the nucleotide sequence of SEQ ID NO:2.

7. A vector for expressing a p53 isoform, comprising a distinct coding element consisting of the polynucleotide of claim 6.

8. A host cell transformed in vitro with the vector of claim 7.

9. The Recombinant p53 isoform produced by the host cell of claim 8.

10. An isolated human isoform of p53, wherein said isoform consists of the amino acid sequence of SEQ ID NO:3.

11. An isolated polynucleotide, wherein said polynucleotide consists of a nucleotide sequence encoding the isoform of claim 10.

12. A vector for expressing a human p53 isoform comprising a distinct coding element consisting of the polynucleotide of claim 11.

13. A host cell transformed in vitro with the vector of claim 12.

14. The Recombinant human p53 isoform produced by the host cell of claim 13.

15. The polynucleotide of claim 11; wherein said polynucleotide consists of the nucleotide sequence of SEQ ID NO:4.

16. A vector for expressing a human p53 isoform, comprising a distinct coding element consisting of the polynucleotide of claim 15.

17. A host cell transformed in vitro with the vector of claim 16.

18. The Recombinant human p53 isoform produced by the host cell of claim 17.

19. A method for controlling the proliferation of cells comprising:

a) transfecting said cells in vitro with the vector of claim 3; and b) allowing the transfected cells of step a) to express the isoform of p53 encoded by said vector, wherein said expression results in an increase or decrease in the proliferation of said cells.

20. A method for controlling the proliferation of cells, comprising:

a) transfecting said cells in vitro with the vector of claim 12; and b) allowing the transfected cells of step a) to express the isoform of p53 encoded by said vector, wherein said expression results in an increase or decrease in the proliferation of said cells.

* * * * *